United States Patent [19]
Tsukaya et al.

[11] Patent Number: 5,279,301
[45] Date of Patent: Jan. 18, 1994

[54] ULTRASONIC IMAGE ANALYZING APPARATUS

[75] Inventors: Takashi Tsukaya, Hachioji; Tatsuya Yamaguchi, Hino; Shuichi Takayama, Hachioji; Masahiko Gondo, Fuchu; Kuniaki Kami, Hachioji, all of Japan

[73] Assignee: Olympus Optical Co., Ltd., Tokyo, Japan

[21] Appl. No.: 790,745

[22] Filed: Nov. 12, 1991

[30] Foreign Application Priority Data

Jan. 18, 1991 [JP] Japan ................. 3-004284
Jan. 18, 1991 [JP] Japan ................. 3-004454
Jan. 18, 1991 [JP] Japan ................. 3-004465

[51] Int. Cl.⁵ .............................. A61B 8/00
[52] U.S. Cl. .................... 128/660.06; 128/660.07
[58] Field of Search ............ 128/660.01, 660.06, 128/660.07; 73/602

[56] References Cited

U.S. PATENT DOCUMENTS

| | | | |
|---|---|---|---|
| 4,817,015 | 3/1989 | Insana et al. | 128/600.01 X |
| 4,817,433 | 4/1989 | Sato | 128/660.04 X |
| 4,852,577 | 8/1989 | Smith et al. | 128/660.07 |
| 5,052,394 | 10/1991 | Carpenter et al. | 128/660.06 |
| 5,095,909 | 3/1992 | Nakayama et al. | 128/660.06 |

Primary Examiner—Francis Jaworski
Attorney, Agent, or Firm—Armstrong, Westerman, Hattori, McLeland & Naughton

[57] ABSTRACT

An ultrasonic image analyzing apparatus determines, on the basis of ultrasonic tomographic image information on a body portion being inspected, the properties of the tissues of the inspected portion, and causes a lesion portion to be displayed on a color image screen or the like, thereby allowing a diagnosis. The apparatus enables appropriate parameters for image analysis which correspond to the object organ, a body mark, and the type of ultrasonic probe used, to be automatically set. The apparatus also enables the size, the shape, the manner of scanning, etc. of regions of interest (ROIs), which are provided on the image of the portion being observed for the purpose of calculating the parameters, to be set in correspondence with the directions in which the ultrasonic wave from the probe propagates. Accordingly, the apparatus makes it possible to perform optimal image analysis with respect to the observation-object portion, and hence, perform correct diagnosis.

13 Claims, 15 Drawing Sheets

ULTRASONIC IMAGE ANALYZING APPARATUS

BACKGROUND OF THE INVENTION

1. Field of the Invention

The present invention relates to an ultrasonic image analyzing apparatus and, more specifically, to an ultrasonic image analyzing apparatus which performs, on the basis of observation image information in an ultrasonic diagnosis system, image analysis of a body portion being observed.

2. Related Background Art

As is well known, an ultrasonic diagnosis system is adapted to determine, on the basis of ultrasonic tomographic image information on a portion being inspected (such as an affected portion of the body), the properties of the tissues of the inspected portion, and to display a lesion portion caused by cancer or the like as a color image on a screen, etc, so as to allow a diagnosis. Also, a great number of proposals have been made concerning diagnosis methods which can be carried out by such a system.

U.S. Pat. No. 4,855,911 describes art entitled "ULTRASONIC TISSUE CHARACTERIZATION", which relates to the following diagnosis method: in an ultrasonic diagnosis system, a scatterer number density (SND) is calculated by obtaining a sum of scatter components from a tissue, and compared with predetermined parameters, thereby determining the properties of the tissue.

U.S. Pat. No. 4,817,015 describes art entitled "HIGH SPEED TEXTURE DISCRIMINATOR FOR ULTRASONIC IMAGING", which relates to the following ultrasonic tissue-property diagnosis method: first, a region of interest (hereinafter abbreviated to "ROI") is set in a portion being inspected, and then, an abnormality of the properties of the tissues is determined on the basis of two of the four parameters consisting of a value b indicating the square of the mean of intensities of the echos reflected from the ROI, a value t indicating a sum of a total average of the backscatter, a noise power spectrum d bar, and an integrated value p of the difference obtained by subtracting a Gaussian noise component from the noise power spectrum d bar.

In recent years, however, while computer image processing has advanced, various efforts have been made, in ultrasonic diagnosis systems, to apply texture analysis to quantitative diagnosis employing endoscopic ultrasonography (hereinafter abbreviated to "EUS") with a view to improving the reliability of the results of diagnosis. For example, an example of such analysis is published in the following Japanese document: "Quantitative Diagnosis Employing Texture Analysis over Ultrasonic-Endoscopic Image (First Report)" (GASTRORENTEROL. ENDOSC. 32:1363-1368, 1990). The above-mentioned EUS is an apparatus which performs scanning of, for example, the inside of an alimentary canal by an ultrasonic probe comprising an ultrasonic vibrator so that an ultrasonic image is obtained to allow diagnosis of an affected portion. An example of a conventional ultrasonic diagnosis system employing such texture analysis will be described with reference to FIG. 15 et seq.

As shown in FIG. 15 (a structural block diagram), an ultrasonic observation apparatus 1, including an ultrasonic scope having an ultrasonic probe, observes a portion being inspected with an ultrasonic wave, and obtains a tomographic image of the inspected portion, which image is displayed on a display 2 consisting of a Tv monitor. A signal outputted from the ultrasonic observation apparatus 1 to the display 2 (alternatively, a signal outputted from a VTR, not shown) is also inputted to an image processing unit 3. The inputted signal is converted into a digital signal by an A/D converter 4, and written into a frame memory 5. The frame memory 5 has, as shown in FIG. 16, a multiplicity of pixels, for example 640×512 pixels, within which a ROI 5A is set, the ROI consisting of, for example, 9×9 pixels, as shown in FIG. 17. A signal from the ROI 5A is inputted to a characteristic amount calculating section 6, which section 6 calculates characteristic amounts of the image.

Said texture analysis is used as a means for calculating such characteristic amounts. Texture analysis per se is already known, as described in, for instance, "Fundamentals of Image Recognition (II)" (a Japanese Document published by Ohm-sha, pages 195 to 200), and includes methods such as a method employing density co-occurrence matrices, a density level difference method, and a density level run-length method and a power spectrum method.

The texture analysis method employing density co-occurrence matrices is fundamentally based on the evaluation of a two-dimensional combined probability density function $f(i, j | d, \theta)$. The function $f(i, j | d, \theta)$ is a probability density function indicating the probability that a pixel which is away from another pixel having a density value i by a distance d in the direction $\theta$, has a density value j. Thus, density co-occurrence matrices express $f(i, j | d, \theta)$ with respect to each $(d, \theta)$ in the form of matrices, and i and j respectively indicate the position of a row and the position of a column. Normally, parameters expressed by the following formulae (1) to (5) are used as effective characteristic amounts:

(i) energy $$E\{S\theta(d)\} = \sum_{i=0}^{NG-1} \sum_{j=0}^{NG-1} \{S\theta(i,j|d)\}^2 \quad (1)$$

(ii) entropy $$H\{S\theta(d)\} = \sum_{i=0}^{NG-1} \sum_{j=0}^{NG-1} S\theta(i,j|d) \log S\theta(i,j|d) \quad (2)$$

(iii) correlation $$C\{\{S\theta(d)\}\} = \frac{\sum_{i=0}^{NG-1} \sum_{j=0}^{NG-1} (i - Vx)(j - Vy) S\theta(i,j|d)}{(\sigma x \sigma y)} \quad (3)$$

(iv) local homogeneity $$L\{\{S\theta(d)\}\} = \sum_{i=0}^{NG-1} \sum_{j=0}^{NG-1} \frac{S\theta(i,j|d)}{1 + (i-j)^2} \quad (4)$$

(v) inertia $$I\{S\theta(d)\} = \sum_{i=0}^{NG-1} \sum_{j=0}^{NG-1} (i-j)^2 \cdot S\theta(i,j|d) \quad (5)$$

In the above formulae, $S\theta(i, j | d)$ represents an element in the row i and in the column j of a matrix $S\theta(d)$, and NG represents the number of density levels of the image. The density averages Vx and Vy, as well as the fractions $\sigma x$ and $\sigma y$ are expressed by the following formulas (6a) to (6d):

$$Vx = \sum_{i=0}^{NG-1} i \sum_{j=0}^{NG-1} S\theta(i,j|d) \quad (6a)$$

$$Vy = \sum_{j=0}^{NG-1} j \sum_{i=0}^{NG-1} S\theta(i,j|d) \quad (6b)$$

$$\sigma x^2 = \sum_{i=0}^{NG-1} (i - Vx)^2 \sum_{j=0}^{NG-1} S\theta(i,j|d) \quad (6c)$$

$$\sigma y^2 = \sum_{j=0}^{NG-1} (j - Vy)^2 \sum_{i=0}^{NG-1} S\theta(i,j|d) \quad (6d)$$

The density level run-length method is a method which may be effectively used when the relevant object is of a certain kind, such as a stripe pattern, whose image can be effectively analyzed by run-length coding. A density level run is a set of pixels which are linearly adjacent to each other and which have the same density value, and its length is the number of pixels contained in the density level run. If a calculation is made as to how many times a run having a density value i and a length j occurs in the $\theta$ direction of the image being processed, and if it is assumed that a density level run matrix R ($\theta$) is a matrix expressing the results of the calculation with respect to each direction $\theta$, the density level run matrix R ($\theta$) is expressed by the following formula where r (i, j|$\theta$) is a matrix element:

$$R(\theta) = [r(i,j|\theta)]$$

Using the above R ($\theta$), the following characteristic amounts are defined as parameters:

(vi) short run emphasis $$RF1\{R(\theta)\} = \frac{\sum_{i=0}^{NG-1} \sum_{j=0}^{NR} \frac{r(i,j|\theta)}{j^2}}{TR} \quad (7)$$

(vii) long run emphasis $$RF2\{R(\theta)\} = \frac{\sum_{i=0}^{NG-1} \sum_{j=1}^{NR} j^2 r(i,j|\theta)}{TR} \quad (8)$$

(viii) array level distribution $$RF3\{R(\theta)\} = \frac{\sum_{i=0}^{NG-1} \left( \sum_{j=1}^{NR} r(i,j|\theta) \right)^2}{TR} \quad (9)$$

(ix) run length distribution $$RF4\{R(\theta)\} = \frac{\sum_{j=1}^{NR} \left( \sum_{i=0}^{NG-1} r(i,j|\theta) \right)^2}{TR} \quad (10)$$

(x) run percentage $$RF5\{R(\theta)\} = \frac{\sum_{i=0}^{NG-1} \left( \sum_{j=1}^{NR} r(i,j|\theta) \right)^2}{TP} \quad (11)$$

where NG represents the number of the density levels, NR represents the number of run lengths in the matrix R($\theta$), TR represents the total number of runs in the direction $\theta$ counted regardless of the length and density value, and TP represents the total number of pixels of the image.

The above description is that of texture analysis. Referring to FIG. 15, the values calculated using the above parameters are compared by a determination section 8 with threshold values $\alpha$ and $\beta$ set in a control section 7 of the processing unit 3 through a keyboard 9 or a track ball 10. If the calculated values are between the threshold values $\alpha$ and $\beta$, a display control section 11 operates for the color display of an image portion corresponding to the ROI 5A so that the values are converted by a D/A converter 12, mixed with a synchronizing (hereinafter abbreviated to "SYNC") signal from a TV SYNC signal generating section 13 by a mixer 14, and displayed on a TV monitor 15. The ROI 5A is moved in up-down and light-right directions to process the whole image. The region to be processed can be set through the keyboard 9 or the track ball 10. When the inside of the body cavity is to be observed by employing the ultrasonic scope, a body mark, consisting of an image illustrating the stomach, the duodenum, the great intestine or the like is simultaneously displayed on the TV monitor screen so that the position of observation is indicated.

Before such image analysis is performed by an ultrasonic image analyzing apparatus, the observer observes a tomographic image of a portion (the object of observation) on the monitor 2. At this time, the observer manually adjusts the density, the sharpness and the luminance of the image so as to facilitate observation by eye. The adjustment has hitherto been effected by an adjusting circuit accommodated in the ultrasonic observation apparatus 1 for adjusting the gain, the contrast and the sensitivity time control (hereinafter abbreviated to "STC") of the output to be transmitted and received from the endoscope.

Also, in the conventional image analyzing apparatus, when calculating the parameters for each ROI set on data on the relevant image, certain fixed size and certain fixed shape of the ROIs are used. Further, the position of ROIs is, at the time of the calculation, scanned by performing scanning in the horizontal and vertical directions on a plane of the image. Furthermore, the parameters are not particularly changed in correspondence with differences in the position of the ROIs.

In the conventional image processor having the above-described function, the parameters for the image analysis have been hitherto set by the operator. That is, it is necessary that parameters for use in calculating characteristic amounts in image analysis be suitably changed in accordance with the object organ or an object body portion being inspected, or the measurement conditions under which the observation apparatus performs observation (such as the type of the ultrasonic probe and the scanning method). Thus, the conventional apparatus has a drawback in that it is difficult to suitably set the parameters if the operator does not have sufficient experience and technical sense.

On the other hand, in the conventional ultrasonic observation apparatus employing the ultrasonic probe, if the probe is, for instance, a mecha-radial scanning type ultrasonic probe 16, such as that shown in FIG. 18, the ultrasonic probe 16 is rotated about a central point O, and the rotation allows tomographic image data in the directions Z in which the ultrasonic wave propagates to be obtained. The ultrasonic probe 16 is secured to the forward end of a flexible shaft 17. If the probe is of an electronic-radial scanning type, vibrator elements are arranged in a circular shape at a forward end, and the vibrator elements to be operated are electrically switched so that, similarly to the case of the mecha-radial type, image data indicating the conditions of the observation-object portion in the ultrasonic-wave propagation directions Z is obtained.

When topological image is obtained by the observation apparatus, the detection width increases with increases in the distance from the ultrasonic probe 16 to the portion being observed (i.e., as the observation-object position becomes relatively farther from the probe to the periphery thereof), thereby causing a reduction in resolution. In addition, as shown in FIG. 19, the beam diameter B has a certain relationship with the distance in each ultrasonic-wave propagation direction Z such that the beam diameter B increases with increases in the distance (i.e., increases at positions away from the position of the probe 16). This also causes the resolution to be lower at peripheral positions than at central positions. Also, the output $|P(f)|$ influenced by the spatial frequency characteristics of the ultrasonic probe 16 is such that, if the position of detection is close, a good characteristic is exhibited in a relatively wide range with respect to the reference frequency $F_0$, as shown in FIG. 20, whereas if the position of detection is distant, great attenuation occurs in a high-frequency range, as shown in FIG. 21. Accordingly, it can be said that there is another risk of the resolution at peripheral positions being lowered.

In view of these risks, the conventional system has other drawbacks. As explained before, when calculating the parameters, the size and the shape of each ROI are fixed, and the position of ROIs is scanned by performing scanning in the horizontal and vertical directions on an image plane. This results in image data, varying in resolution, being subjected to the same processing. As a result, the calculation inevitably involves unnecessary calculating operations, thereby rendering the system disadvantageous in terms of time and level of precision. Furthermore, since the resolution is high at positions close to the ultrasonic probe 16, the probe 16 is usually brought into a position close to the portion to be observed. However, the conventional system performs the same processing regardless of the distance from the probe, thus failing to be favorable in terms of the level of precision.

When determining the structure of the tissues of the portion being observed, those calculated values of parameters, among calculated values of parameters such as the above-described short run emphasis and the long run emphasis, which lie between predetermined threshold values are used as characteristic amounts, and the tissue structure is determined from a combination of the parameters. However, in the conventional system, no consideration is given to the contribution ratio of parameters with respect to the calculation threshold values therefor, the combinations thereof and the determination based thereon, nor is consideration given to using calculation formulae including information on how far the object portion is from the ultrasonic probe 16. As a result, it has been difficult to realize correct determination and appropriate processing with respect to all of the regions of image data having different levels of resolution.

Before image analysis processing takes place in the conventional image analyzing apparatus, the gain, contrast and STC of the output to be transmitted and received from the endoscope is, as described before, adjusted by the observer (who specifies the density, etc. of the image) through the adjusting circuit provided within the observation apparatus 1. However, since this image adjustment is liable to be influenced by perception of individual operators, the condition created by the image adjustment cannot always be optimal to the image processing, such as texture analysis, which follows the adjustment.

SUMMARY OF THE INVENTION

A first object of the present invention is to provide an ultrasonic image analyzing apparatus capable of automatically setting parameters for image analysis (which parameters have hitherto been arbitrarily set by the operator) on the basis of the organ being observed (i.e., the object of observation), a body mark indicating the object portion being observed, and information on the measurement environment of the ultrasonic observation apparatus, the environment determining the conditions of the image observation and including environmental conditions, such as the type of the ultrasonic probe used in the observation, which can influence the calculation of characteristic amounts. The apparatus is thus capable of calculating characteristic amounts in image analysis with a higher level of accuracy.

A second object of the present invention is to provide an ultrasonic image analyzing apparatus capable of varying, in correspondence with the directions and the distance in and over which the ultrasonic wave from the ultrasonic probe propagates, parameters for image analysis and/or the size, the shape, and the scanning method of ROIs. The apparatus is thus capable of performing image analysis by detecting image characteristic amounts at high levels of efficiency and precision.

A third object of the present invention is to provide an ultrasonic observation apparatus which is, when performing computer image processing, capable of outputting an image signal which is suitable for signal analysis and which can remain unchanged by at least the adjustment of gain, contrast and STC.

In order to achieve the first object, the present invention provides an ultrasonic image analyzing apparatus in an ultrasonic diagnosis system, the apparatus performing, on the basis of observation image information outputted from an ultrasonic observation apparatus, image analysis of an observation-object portion being observed, the image analyzing apparatus comprising: an image storing means for inputting image information on the observation-object portion obtained by performing scanning with an ultrasonic probe, and for storing the image information; a parameter storing means for storing a plurality of parameters for image analysis which correspond to the measurement environment of the ultrasonic observation apparatus and/or the observation-object portion; an image analysis control means for automatically selecting, from among the plurality of parameters, those parameters appropriate to the measurement environment, either automatically or manually specified, and/or the observation-object portion, and for specifying regions of interest (ROIs) on a plane of an image of the observation-object portion; and a characteristic amount calculating means for calculating characteristic amounts indicative of the structure and the properties of the observation-object portion by analyzing, using the selected parameters, the image of the observation-object portion with respect to each of the ROIs.

With the above-specified ultrasonic image analyzing apparatus, parameters for image analysis, which have hitherto been manually and arbitrarily set, are automatically set in correspondence with, for instance, the object organ, a body mark, and the type of the scope used. Accordingly, it is possible to perform optimal image analysis, and correct diagnosis.

In order to achieve the second object, the present invention provides an ultrasonic image analyzing apparatus in an ultrasonic diagnosis system, the apparatus performing, on the basis of observation image information outputted from an ultrasonic observation apparatus, image analysis of an observation-object portion being observed, the image analyzing apparatus comprising: an image storing means for inputting image information on the observation-object portion obtained by performing radial scanning with an ultrasonic probe, and for storing the image information; an image analysis control means for specifying parameters for image analysis and/or ROIs while varying the parameters and/or the ROIs in correspondence with the directions in which the ultrasonic wave from the ultrasonic probe propagates; and a characteristic amount calculating means for calculating characteristic amounts indicative of the structure and the properties of the observation-object portion by analyzing, using the parameters for image analysis, an image of the observation-object portion with respect to each of the ROIs of the observation-object portion.

With the above-specified image analyzing apparatus, parameters for image analysis and/or the size of the ROIs is varied in accordance with various positions of the observation-object portion. Therefore, it is possible to perform image analysis while giving consideration to the level of resolution, the S/N ratio, STC, etc. of the radial scanning with the ultrasonic probe, thereby enabling more precise image analysis. Furthermore, the frame rate can be improved.

In order to achieve the third object, the present invention provides an ultrasonic observation apparatus in an ultrasonic diagnosis system, the apparatus supplying observation image information for image analysis to an ultrasonic image analyzing apparatus for performing image analysis of an observation-object portion being observed, the ultrasonic observation apparatus comprising: a gain, contrast and sensitivity time control (STC) adjusting means for inputting image information on the observation-object portion obtained by performing scanning with an ultrasonic probe, the means being capable of adjusting the gain, the contrast and the STC of the image information; and an image signal outputting means for enabling image information in which at least one of the gain, the contrast and the STC is in a state equivalent to the unadjusted state, to be outputted as image information for signal analysis.

With the above-specified ultrasonic observation apparatus, a means is provided for outputting an image signal for signal analysis, which image signal can remain unchanged by the adjustment of gain, contrast and STC. Therefore, even if change(s) have been made in the observation image output, when supplying image data to the image analyzing apparatus, it is possible to output image data which is always equivalent to the unchanged original data. Thus, it is possible to output image data which is highly precise and which has a highly precise reproducibility.

DETAILED DESCRIPTION OF PREFERRED EMBODIMENTS

Figure 1:
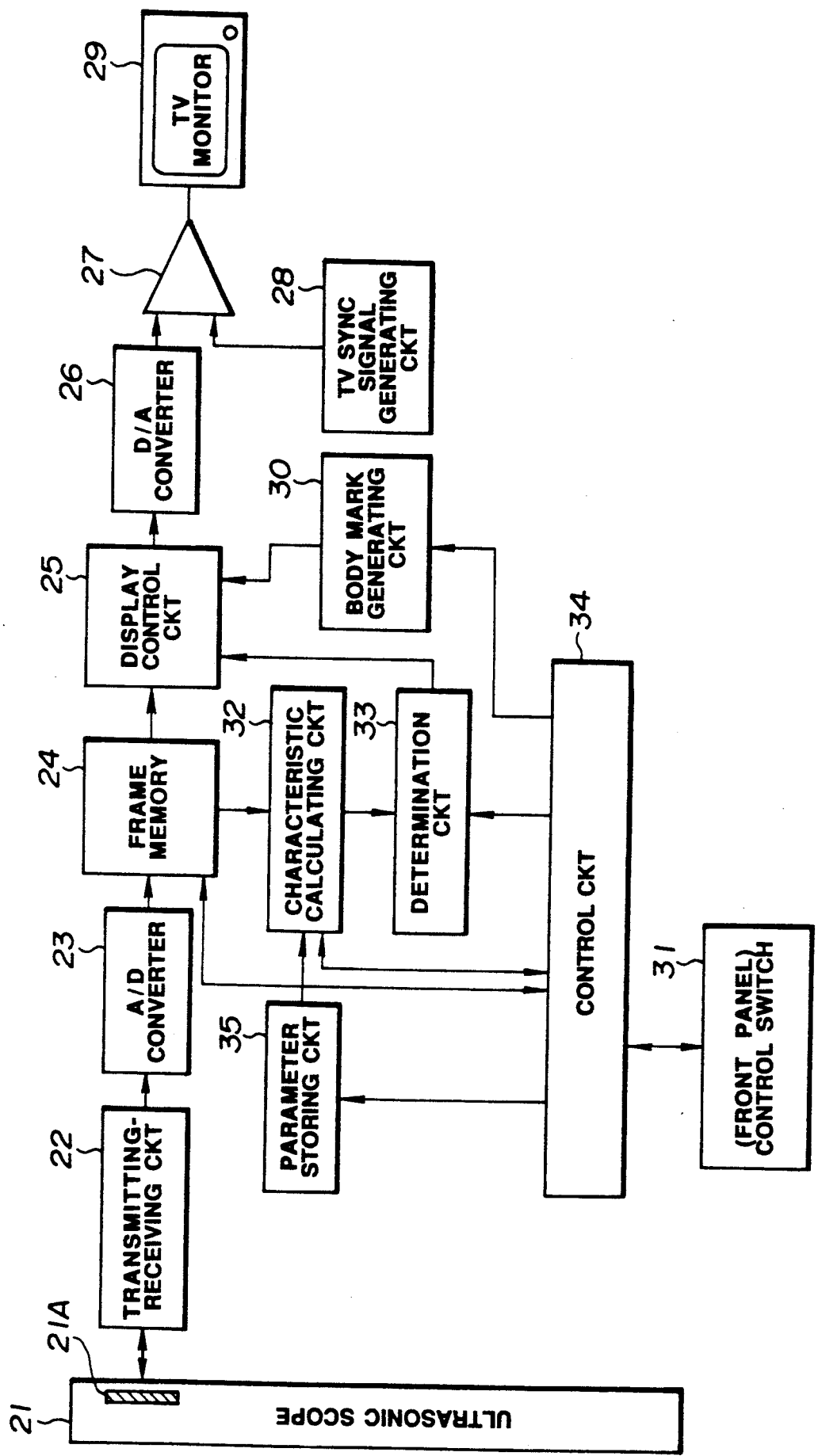
FIG. 1 is a structural block diagram of an ultrasonic image analyzing apparatus, showing a first embodiment of the present invention.

The present invention will be specifically described below with respect to certain embodiments thereof shown in the drawings.

FIG. 1 illustrates a first embodiment of the present invention. An ultrasonic scope 21, serving as an ultrasonic observation apparatus, has, and accommodates therein, an ultrasonic probe 21A comprising an ultrasonic vibrator. An exciting voltage is applied to the probe 21A from a transmitting-receiving circuit 22 (the term "circuit" is abbreviated to "ckt" in the drawings; this applies to other circuits, described below), so that an ultrasonic wave is radiated onto the inside of the body cavity (the object of inspection), such as an affected portion of the stomach. Wave reflected from the inspection object is received by the ultrasonic vibrator, and inputted to the transmitting-receiving circuit 22, whereby the inputted wave is amplified, has its gain and contrast adjusted, and then detected.

Subsequently, the output resulting from this detection is converted into digital data by an A/D converter 23. After the digital data is subjected to interpolation and like processes, the data is written into a frame memory 24 serving as an image information storing means 24. An output of the frame memory 24 is passed through a display control circuit 25 and a D/A converter 26, then mixed with a SYNC signal from the TV SYNC signal generating circuit 28 by a mixer 27, and then displayed on a TV monitor 29. At this time, a body mark indicating the portion being observed is also displayed on the monitor 29 simultaneously with the image from the frame memory 24.

Such a body mark is generated by a body mark generating circuit 30 serving as a body mark display means, and is superimposed on the image from the frame memory by the display control circuit 25. A control switch 31 provided on a front panel allows the body mark to be selected.

The image data is also outputted from the frame memory 24 to a characteristic amount calculating circuit 32 serving as a characteristic amount calculating means. After the calculating circuit 32 has calculated characteristic amounts by employing a texture analysis method, such as described in the previous section, a determination circuit 33 compares each of the amounts with threshold values already specified and inputted through a control circuit 34 to the determination circuit 33. Subsequently, various portions of the data which correspond to differences in properties of the tissues are colored by the display control circuit 25, and the colored image data is displayed on the TV monitor 29.

As described before, it is necessary that parameters used to calculate the characteristic amounts be varied in correspondence with the portion being observed, the object organ, and other factors. According to this embodiment, a parameter storing circuit 35, serving as a parameter storing means, is provided to store a plurality of parameters corresponding to body marks that can be displayed on the TV monitor 29, and optimal parameters are automatically selected and set by the control circuit 34 serving as an image analysis control means. The control circuit 34 scans a plane of observation image, and calculates the values of the parameters with respect to each of specified ROIs, so as to calculate the characterizing amounts.

Specifically, when one of the body marks is selected through the control switch 31 on the front panel, the control circuit 34 causes certain parameters which correspond to the object organ indicated by the selected body mark to be simultaneously selected from among the parameters stored in the parameter storing circuit 35. The selected parameters are used in the calculation of the characteristic amounts by the characteristic amount calculating circuit 32.

According to this embodiment, therefore, setting of parameters that are optimal to the portion being observed can be effected automatically and very easily only by setting a certain body mark. Although in the above-described embodiment, parameters optimal to the portion being observed are set mainly in accordance with a particular body mark, it is also possible to provide an ultrasonic image analyzing apparatus where, as will be described later, parameters which correspond to condition(s) other than those determined by the portion being observed (such as measurement environment determining the measurement conditions of the observation apparatus and including the type and the scanning method of ultrasonic probe, or information on the resolution, or the like) are either automatically selected or set by manually inputting such information, etc. through the control switch, the apparatus thus being capable of obtaining more accurate characteristic amounts. In the above-described embodiment, although the size and the shape of the ROIs may be fixed, as in the conventional apparatus, and the scanning direction of the ROIs may be such that scanning is performed on the plane of the image in the horizontal and vertical directions, the scanning direction, the size and the shape of the ROIs may be determined in accordance with the ultrasonic probe used, as will be described later in a third embodiment and modifications thereof.

Figure 2:
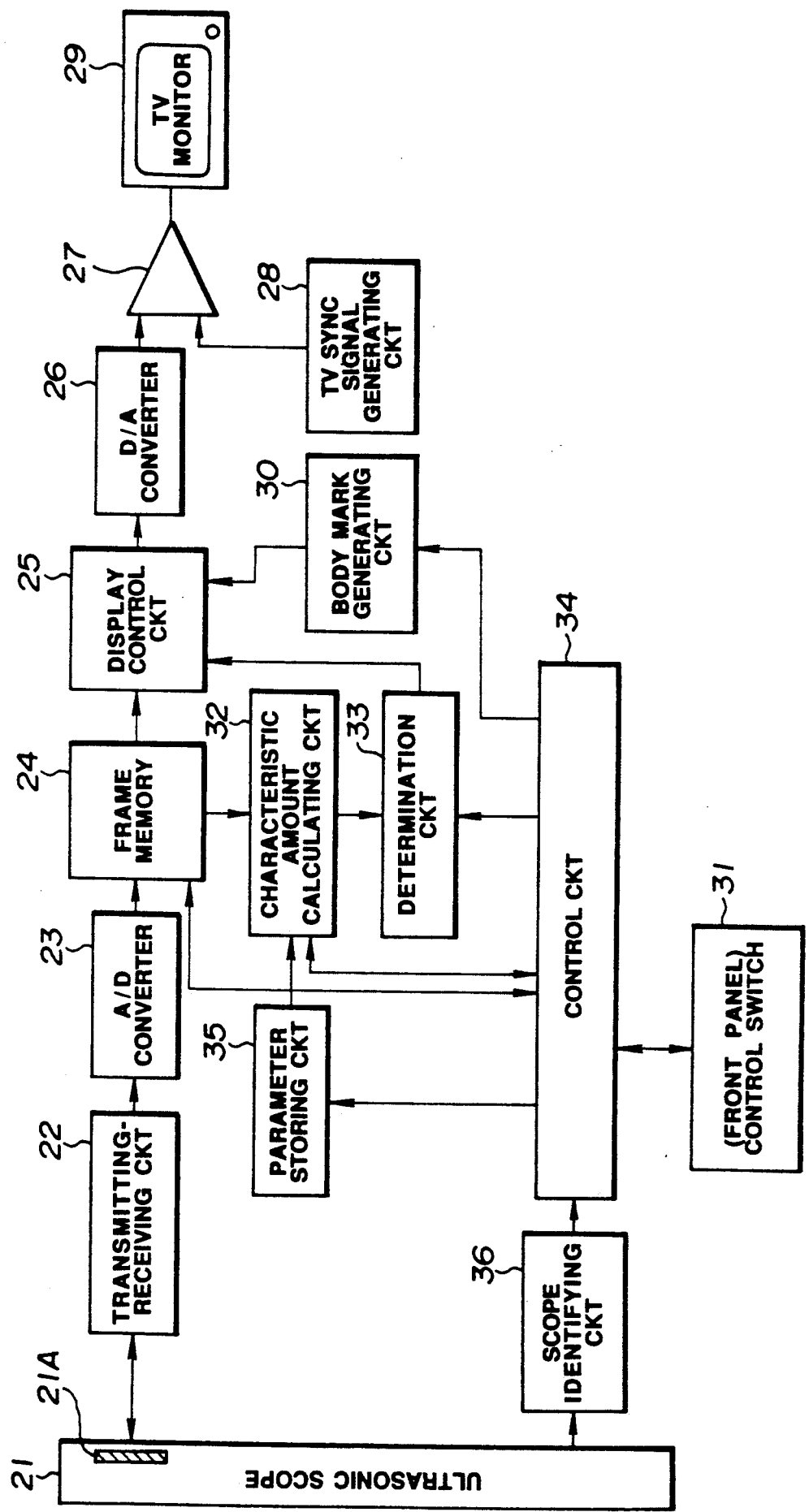
FIG. 2 is a structural block diagram of an ultrasonic image analyzing apparatus, showing a second embodiment of the present invention.

FIG. 2 is a structural block diagram of an ultrasonic image analyzing apparatus, showing a second embodiment of the present invention. The second embodiment is adapted to distinguish the type of the ultrasonic scope serving as the associated ultrasonic observation apparatus by distinguishing, for instance, the type of the ultrasonic probe provided in the scope, and to automatically set, on the basis of an output resulting from this distinction, parameters corresponding to the probe type.

Specifically, as shown in FIG. 2, a scope identifying circuit 36, serving as a scope identifying means for identifying the type of the ultrasonic scope 21 used, is provided, and a plurality of parameters which correspond to various types of scope are already stored in a parameter storing circuit 35. The other construction of the second embodiment is exactly the same as that of the image analyzing apparatus according to the first embodiment.

With the image analyzing apparatus according to the second embodiment having the above-described construction, the type of the scope 21 (in this case, the type of the ultrasonic probe 21A) is identified by the scope identifying circuit 36, and a signal indicating this identification is inputted via the control circuit 34 to the parameter storing circuit 35, which allows parameters corresponding to the type of the scope 21 to be selected. The selected parameters are set in the characteristic amount calculating circuit 32.

Thus, according to the second embodiment, on the basis of an output of the scope identifying circuit 36, parameters which correspond to the scope used are automatically set, thereby enabling optimal image analysis to be performed. The parameters already stored in the parameter storing circuit 35 may be parameters corresponding to organs or portions which can be observed with the scope. Further, a body mark may be automatically selected in correspondence with the type of scope.

Although not shown, the image analyzing apparatus according to the first or second embodiment may be modified in the following manner: The results of calculation performed by the characteristic amount calculating circuit 32 (shown in FIG. 1 or FIG. 2) are compared with parameters in the parameter storing circuit 35 which indicate the characteristics of various organs; and parameters appropriate for the determination of the tissue properties of the object organ are selected from the parameter storing circuit 35.

Further, the results detected by using the parameters indicating the characteristics of various organs may be displayed on the same image screen. The parameters indicating the characteristics of various organs may be successively switched, and detection may be performed with respect to a plurality of different organs. The parameters may be changed in accordance with the lesion portion whose inspection is desired. The STC, the gain and the contrast of the received signal may be automatically set in correspondence with the organ, the lesion portion, the type of scope, the body mark, and/or the parameters.

Another ultrasonic image analyzing apparatus embodying a third embodiment of the present invention will be described. The image analyzing apparatus is similar to the image analyzing apparatus according to the first embodiment in that an ultrasonic probe is employed, an image of a portion being observed is analyzed by texture analysis, and characteristic amounts of the image are calculated. However, in contrast with the image analyzing apparatus according to first embodiment where the calculation employing the parameters is performed with respect to each of ROIs the size and the shape of which are fixed and which are scanned by performing scanning on the plane of the image in the horizontal and vertical directions, the third embodiment is distinguished in that, when performing calculation of parameters, the size and the shape of the ROIs are suitably varied, and the position of the ROIs is scanned by performing scanning along concentric circles on the plane of the image.

Figure 3:
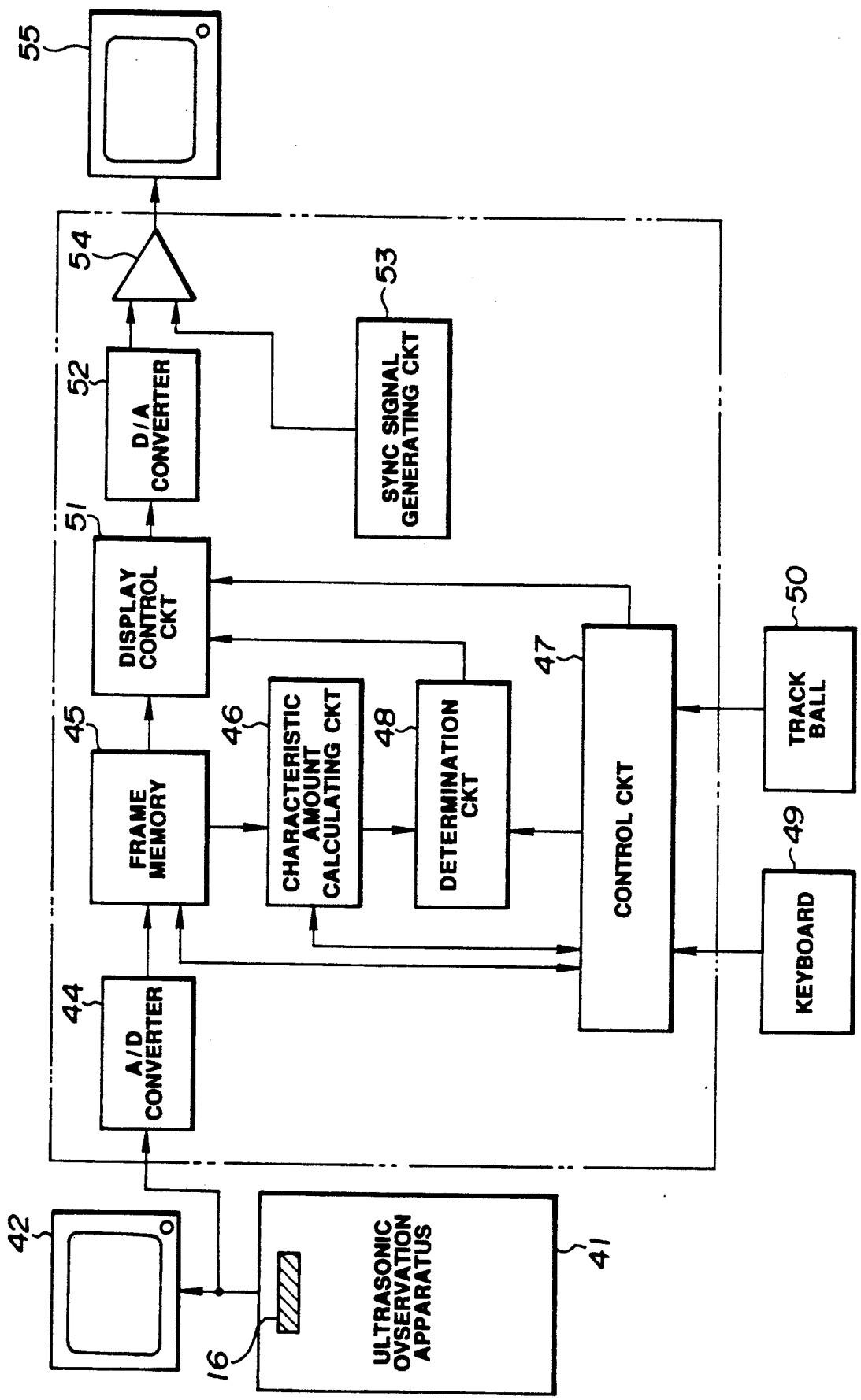
FIG. 3 is a structural block diagram of an ultrasonic image analyzing apparatus, showing a third embodiment of the present invention.

The construction of the image analyzing apparatus according to this embodiment basically comprises, as shown in FIG. 3, an ultrasonic observation apparatus 41, an observation monitor 42 associated with the observation apparatus 42, a processing unit 43, a keyboard 49 and a track ball 50 through which specific values concerning ROIs, parameters and the like are inputted, and a monitor 55 of the analyzing apparatus.

Figure 18:
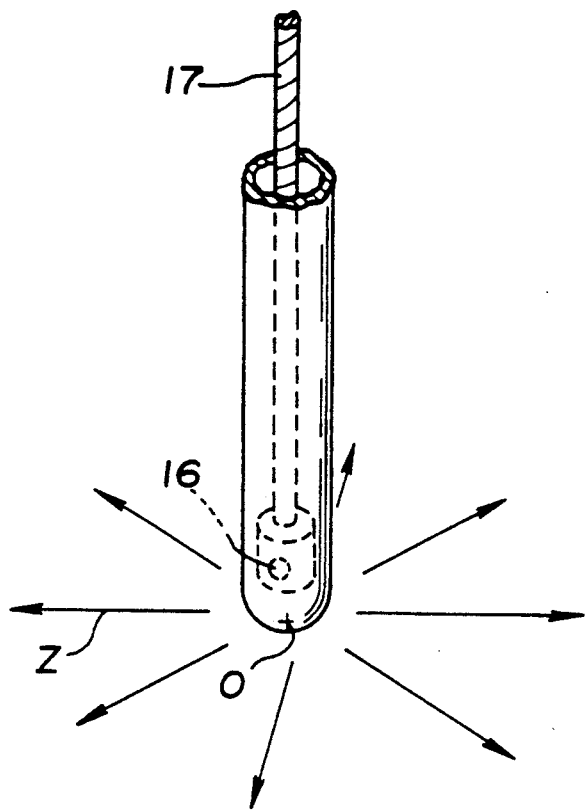
FIG. 18 is a perspective view of an ultrasonic probe for radial scanning, the probe being incorporated in the ultrasonic image analyzing apparatus shown in FIG. 15.
Figure 19:
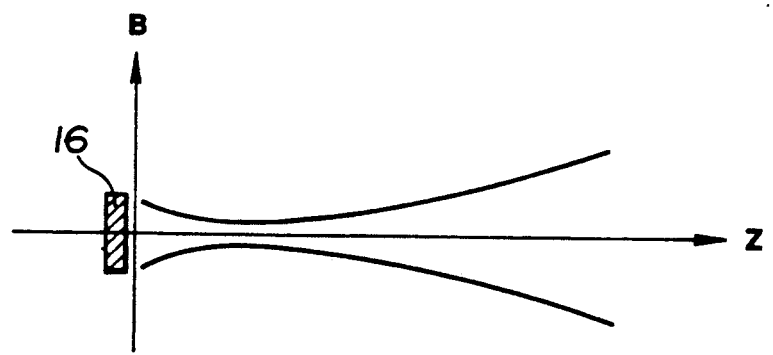
FIG. 19 is a diagram showing changes in the width of the beam from the ultrasonic probe shown in FIG. 18.
Figure 20:
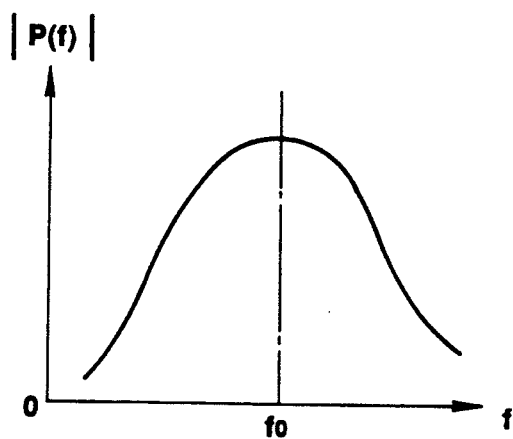
FIG. 20 is a diagram showing the spatial frequency characteristic of a short-distance output of the ultrasonic probe shown in FIG. 18.
Figure 21:
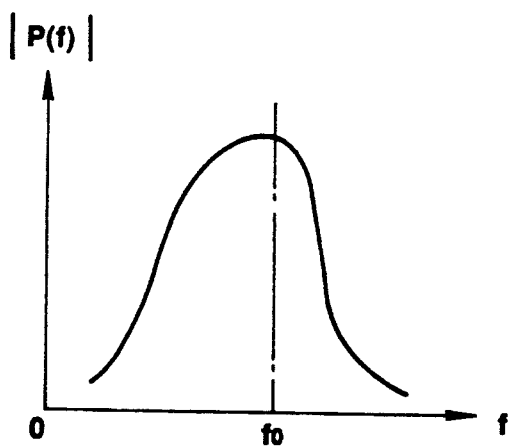
FIG. 21 is a diagram showing the spatial frequency characteristic of a long-distance output of the ultrasonic probe shown in FIG. 18.

The ultrasonic observation apparatus 41 has an ultrasonic probe 16 which can be, for instance, inserted into a body canal or a body cavity for performing radial scanning, such as that shown in FIG. 18. The processing unit 43 has various components whose operation is controlled by a control circuit 47. The unit 43 inputs an output of the observation apparatus, performs texture analysis on the basis of data indicated by the output, and outputs the results of the analysis to the color monitor 55.

Specifically, an output of the observation apparatus 41 resulting from observation thereby is subjected to A/D conversion by an A/D converter 44. The output of the converter 44 is inputted to a frame memory 45 (serving as an image information storing means), in which the output is stored as image data. A characteristic amount calculating circuit 46 extracts image data from an area corresponding to a particular ROI already specified by a control circuit 47 serving as an image analysis control means, and the circuit 46, serving as a characteristic amount calculating means, calculates the values of parameters already selected by the control circuit 47 by utilizing calculation formula concerning, for example, the short run emphasis and the long run emphasis described in the previous section, thereby calculating characteristic amounts.

Subsequently, a determination circuit 48 subjects the characteristic amounts to a certain determination process employing threshold values $\alpha$ and $\beta$ serving as determination reference separately specified by the determination circuit 48. On the basis of the results of the determination, the properties as well as the tissue structure of a portion being observed are determined, so that a diagnosis may be given determining the name of the lesion, etc. The determination results are outputted to a display control circuit 51. The display control circuit 51 superimposes the results of the image analysis on the image output from the frame memory 45. A D/A converter 52 performs D/A conversion of the thus obtained output of the circuit 51, and a mixing and amplifying circuit 54 causes the converted output to be mixed with a signal from a video SYNC signal generating circuit 53. Then, the color monitor 55 for displaying the results of the image analysis performs color display.

Figure 4:
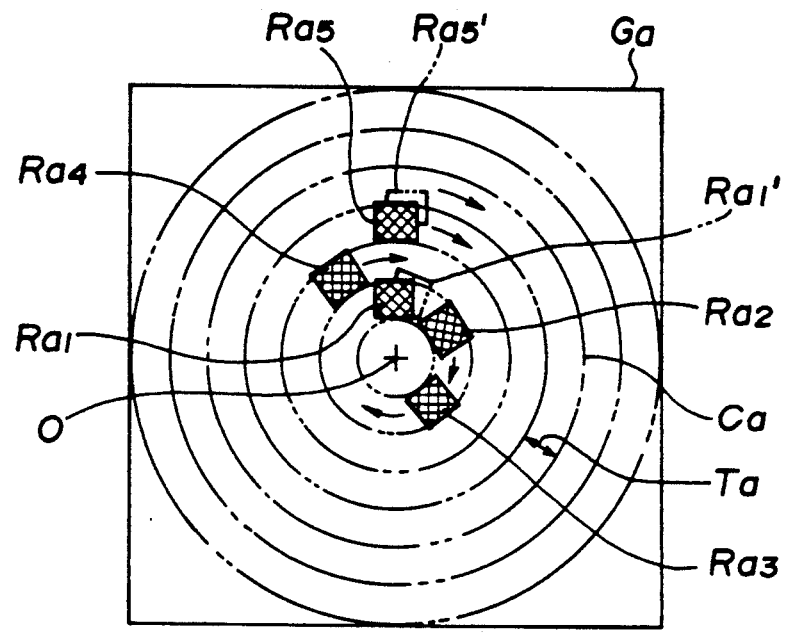
FIG. 4 is a diagram showing the scanning of ROIs on an analysis processing plane performed by an ultrasonic image analyzing apparatus shown in FIG. 3.
Figure 5:
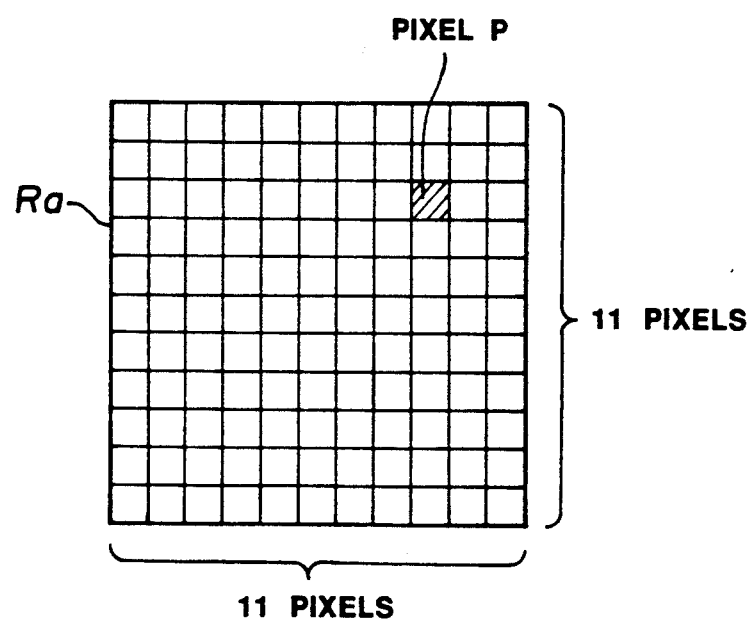
FIG. 5 is a diagram showing each ROI during image analysis processing by the ultrasonic image analyzing apparatus shown in FIG. 3.

FIG. 4 shows a state of scanning ROIs on an image plane Ga during the image processing by the image analyzing apparatus according to this embodiment. On the image plane shown in FIG. 4, it is assumed that the ultrasonic probe 16 rotates about a central point 0. ROIs used in texture analysis performed by the apparatus according to this embodiment are areas arranged around the position 0 and located on circular arcs Ca spaced from each other by a substantially constant width Ta in the radial directions coincident with the ultrasonic-wave propagation directions Z. Each area is a substantially rectangular area whose circumferential dimension is also determined to be a certain width. The size of each ROI (Ra1, Ra2, ... ) is set as, for instance, the size sufficient for defining a 11 pixel by 11 pixel area (see FIG. 5).

The values of the parameters is calculated in the following manner: The calculation with respect to specified ROIs starts at a position in the center of the image plane. Sequential parameter value calculation is performed while some of the ROIs are sequentially scanned (that is, the region of current interest is moved) along a first circumference described with a first radius, the amount of the movement being approximately equal to the circumferential dimension of one pixel. For instance, in the case shown in FIG. 4, movement for sequential scanning takes place from a region Ra1 to a subsequent region Ra1'. When the movement has been completed with respect to the first circumference, the radius is increased by one pitch (by the radial width Ta), and parameter value calculation is performed with respect to the ROIs on the subsequent circumference. The parameters for ROIs (e.g., Ra1, Ra2 and Ra3) whose positions are the same radius distant from the center O are not varied between the ROIs. However, with respect to ROIs (e.g., Ra4, Ra5, etc.) whose positions are different radii distant from the center O, values are calculated employing parameters which are varied in correspondence with the resolution of the measurement data.

Although in the above-described example, the radius is increased by one pitch (Ta) after the ROI scanning has been completed with respect to one circumference, the radius may be increased by one pixel (e.g., from Ra 5 to Ra5'). In this way, it is possible to more accurately calculate the values of the parameters. In the peripheral portion, it is not always necessary to perform parameter value calculation.

There are several possible methods of varying the parameters such as: varying the threshold values for determining the characteristic amounts; varying the ratio at which parameters for determining the properties of the observed portion are combined; or varying the parameter calculation formulae per se.

As described above, according to this embodiment, calculation starts with the processing of a central portion of the image plane where the resolution is high, and the peripheral portion, which is of less importance to the diagnosis, is processed within a shortest period of time as possible. This makes it possible to increase the frame rate. Further, since the parameters are varied in correspondence with the distance from the center, it is possible to render the calculation less influenced by variations in the resolution, the S/N ratio and STC.

Figure 6:
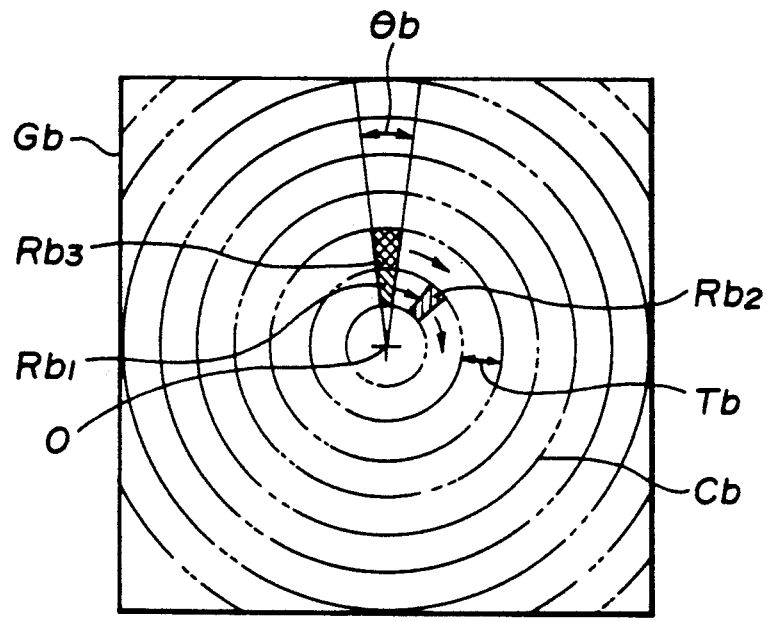
FIG. 6 is a diagram showing the scanning of ROIs on an analysis processing plane performed in a modification of an image analysis control means of the ultrasonic image analyzing apparatus according to the third embodiment.

FIG. 6 shows ROIs (Rb1, Rb2 and Rb3) on a plane Gb of the image being processed in a modification of the image analysis control means of the ultrasonic image analyzing apparatus according to the third embodiment. An image analyzing apparatus to which the modification is applied has the same construction as the image analyzing apparatus (third embodiment) shown in FIG. 3.

Figure 7:
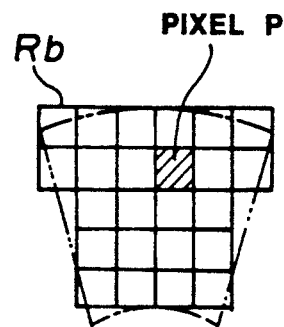
FIG. 7 is a diagram showing each ROI for image analysis by the modification shown in FIG. 6.

In this modification, ROIs are areas having a shape obtained by defining the areas by (i) circular arcs Cb spaced from each other by a constant radial width Tb and (ii) a unit sector angle θb corresponding to the radial scanning of the ultrasonic probe 16. The center O of the circular arcs Cb coincides with the position of the ultrasonic probe. FIG. 7 shows each of the ROIs at an enlarged scale, more specifically, a fan shape of each ROI (Rb) composed of a plurality of pixels P. During texture analysis, when scanning the ROIs for the purpose of parameter value calculation, the scanning is performed first from an inner position along the same circumference, and then toward positions on outer circumferences.

In this modification, since each ROI is a fan-shaped unit, the unit, when compared with that of the third embodiment, enables better correspondence to variations in the resolution in the directions Z in which the ultrasonic wave from the ultrasonic probe 16 propagates. This is because the ROIs have smaller dimensions on inner circumferences where the resolution is high, and the ROIs have greater dimensions on outer circumferences where the resolution is low. Therefore, it is possible to further improve the precision of analysis, and also to curtail the period required for observation. The ROI scanning may be performed from a position on an outer circumference.

Figure 8:
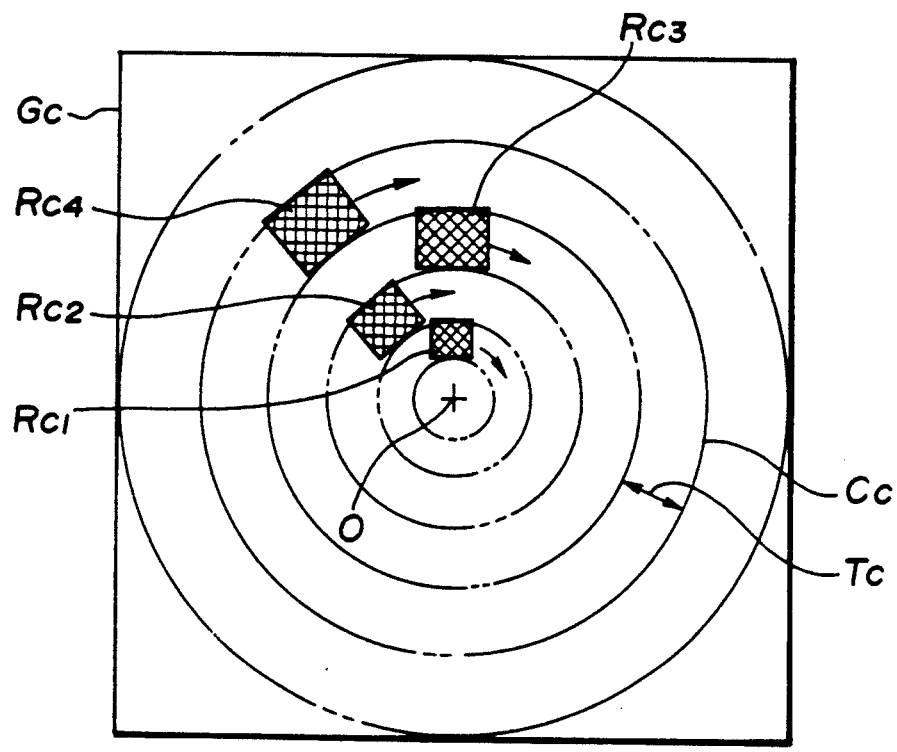
FIG. 8 is a diagram showing the scanning of ROIs on an analysis processing plane performed in another modification of an image analysis control means of the ultrasonic image analyzing apparatus according to the third embodiment.

FIG. 8 shows ROIs (Rc1, Rc2, Rc3 and Rc4) on a plane Gc of the image being processed in another modification of the image analysis control means of the ultrasonic image analyzing apparatus according to the third embodiment. An image analyzing apparatus to which the second modification is applied has the same construction as the image analyzing apparatus (third embodiment) shown in FIG. 3.

In this modification, the shape of ROIs is similar to that in the third embodiment, that is, a rectangular shape defined between parts of two adjacent circular arcs Cc described about the center O of rotation of the ultrasonic probe 16. However, the modification is distinguished in that the radial width Tc between two adjacent circular arcs Cc is decreased with decreases in the distance of the circular arcs Cc from the center O, and the circumferential width of the ROIs is also decreased with decreases in the distance from the center O. As a result, the ROIs have greater areas as their position shifts toward the periphery.

When scanning the ROIs, those ROIs on inner circumferences and with smaller rectangular areas are scanned with smaller amounts of movement, thereby increasing the precision of analysis. In contrast, the amount of movement for the scanning is increased at peripheral positions, thereby lowering the precision of detection in accordance with variations in the level of resolution, etc. This makes it possible to perform image analysis which entails only a slight reduction in the frame rate.

Figure 9:
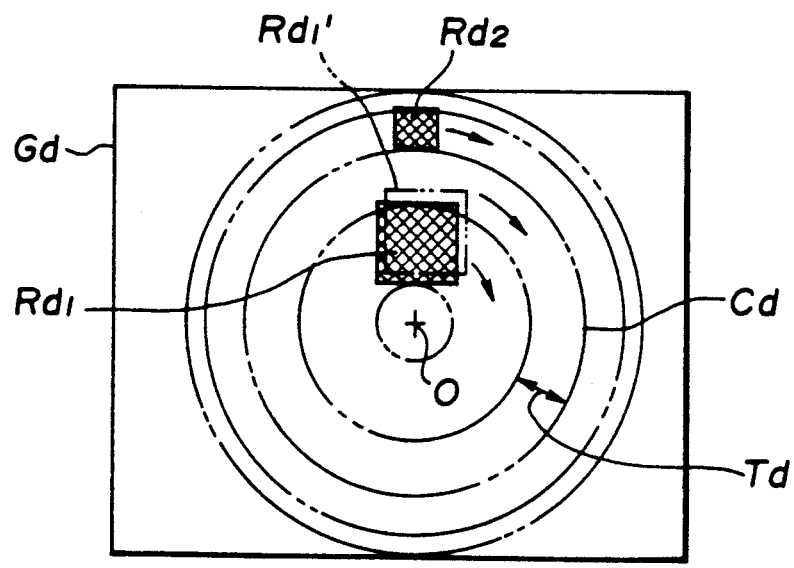
FIG. 9 is a diagram showing the scanning of ROIs on an analysis processing plane performed in a further modification of an image analysis control means of the ultrasonic image analyzing apparatus according to the third embodiment.

FIG. 9 shows ROIs (Rd1, Rd2 and Rd3) on a plane Gd of the image being processed in a further modification of the image analysis control means of the ultrasonic image analyzing apparatus according to the third embodiment. In this modification, the shape of ROIs is similar to that in the third embodiment, that is, a rectangular shape defined between parts of two adjacent circular arcs Cc described about the center O of rotation of the ultrasonic probe 16. However, the modification is distinguished in that the radial width Td between two adjacent circular arcs Cd is decreased with increases in the distance of the circular arcs Cd from the center O, and the circumferential width of the ROIs is also decreased with increases in the distance from the center O. As a result, the ROIs have smaller areas as their position shifts toward the periphery.

When scanning the ROIs, those ROIs on inner circumferences and with greater rectangular areas are scanned with smaller amounts of movement (e.g., from a region Rd1 to a subsequent region Rd1'), thereby increasing the precision of analysis within a relatively wide range. In contrast, the amount of movement for the scanning is increased at peripheral positions, thereby lowering the precision of detection in accordance with variations in the level of resolution, etc, so that efficient analysis is possible.

Although in the modifications shown in FIG. 6, FIG. 8 and FIG. 9, the shape of the ROIs is varied in accordance with the directions of the propagation of the ultrasonic wave, the parameters may simultaneously be varied, thereby further increasing the precision of analysis. Alternatively, the shape of the ROIs may be unchanged while only the parameters are varied. Further, the scanning may be performed by moving the ROIs in the ultrasonic-wave propagation directions first, and then moving them in the circumferential directions.

Figure 10:
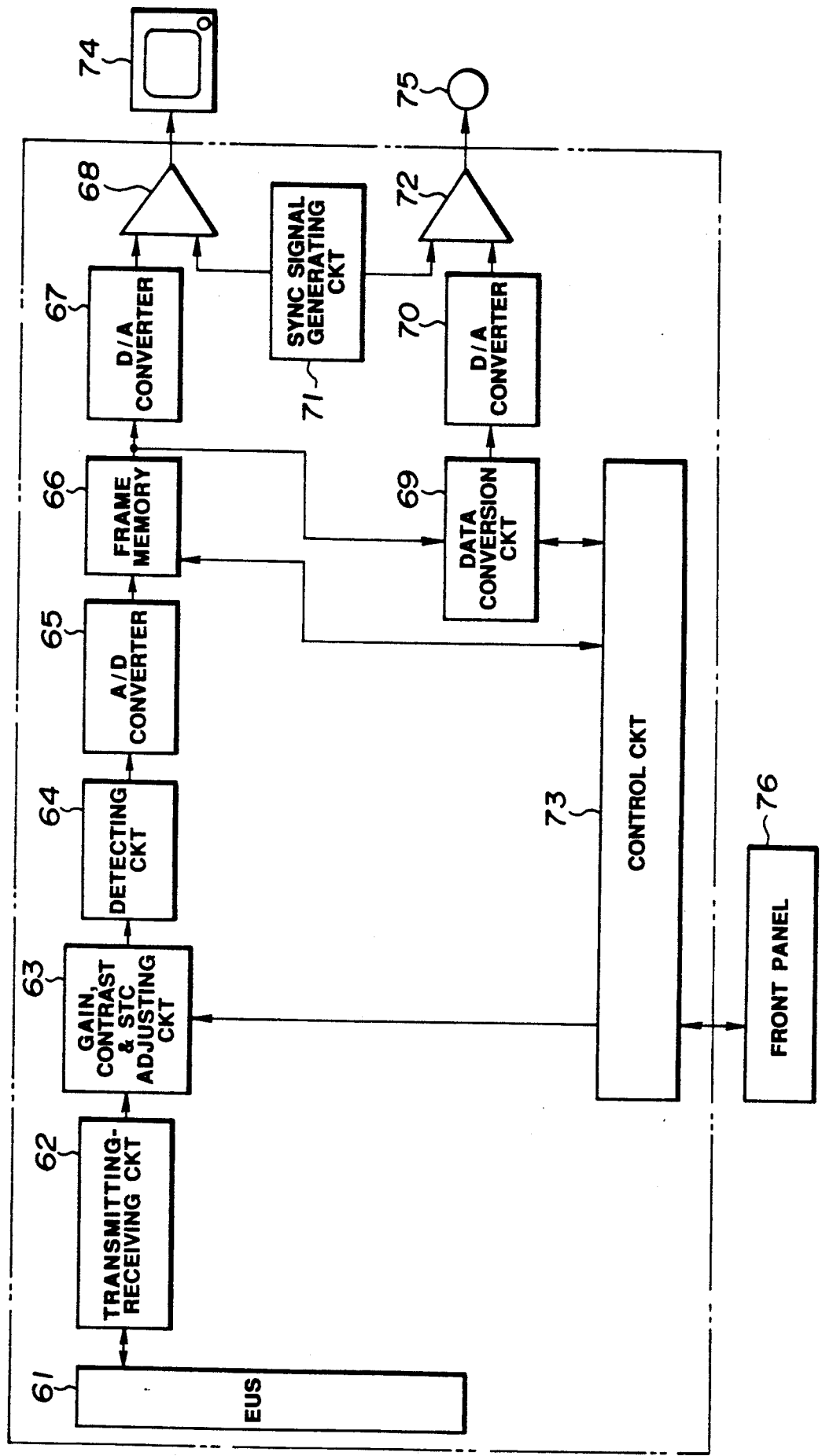
FIG. 10 is a structural block diagram of an ultrasonic observation apparatus, showing a fourth embodiment of the present invention.

FIG. 10 is a structural block diagram of an ultrasonic observation apparatus, showing a fourth embodiment of the present invention. The ultrasonic observation apparatus is an apparatus capable of displaying image information on a portion being observed onto a monitor, and also capable of outputting image information to, for instance, the characteristic amount calculating circuit 32 for image analysis (included in the image analyzing apparatus according to the first embodiment shown in FIG. 1), or the characteristic amount calculating circuit 46 (included in the image analyzing apparatus according to the third embodiment shown in FIG. 3).

As shown in FIG. 10, the observation apparatus includes an EUS 61, serving as an endoscopic ultrasonography means, and a frame memory 66, serving as an image information storing means, which memory inputs a tomographic image observation output of the EUS 61. The image information on a portion being observed is outputted to a video monitor 74 for the purpose of observation, and also to a image data output terminal 75 for the purpose of image analysis.

More specifically, in the ultrasonic observation apparatus, an exciting voltage is applied to an ultrasonic probe (comprising ultrasonic vibrator) of the EUS 61 via a transmitting-receiving circuit 62, so that an ultrasonic beam is generated. The beam is radiated onto an object of inspection. Wave reflected from the inspection object is received by the ultrasonic probe. A tomographic observation output of the probe is inputted via the transmitting-receiving circuit 62 to a gain, contrast and STC adjusting circuit 63, serving as a gain contrast and STC adjusting means, which is controlled by a control circuit 73. The gain, contrast and STC adjusting circuit 63 performs, through the control circuit 73, the adjustment of the gain, the contrast and the STC of the probe output in accordance with the specification given by the observer through a front panel 76. The output of the adjusting circuit 63 is detected by a detecting circuit 64, subjected to A/D conversion by an A/D converter 65, and, after subjected to interpolation and the like, stored in the frame memory 66. During the observation of a tomographic image, image data from the frame memory 66 is D/A-converted by a D/A converter 67, mixed with an output of a video SYNC signal generating circuit 71 by a mixing circuit 68, and outputted to the external video monitor 74.

The apparatus also includes a data conversion circuit 69, serving as a means for outputting a signal for signal analysis. The circuit 69 subjects image data from the frame memory 66 to a data conversion process in which the quantities changed as a result of the adjusting by the gain, contrast and STC adjusting circuit 63 are caused to recover their original values on the basis of a command from the control circuit 73. The above-mentioned original values are values indicating image data adjusted in accordance with certain gain, contrast and STC values which have been previously determined in such a manner as to increase the precision of analysis during image processing for processing the image data on the portion being observed. The three types of values consisting of the gain value, the contrast value and the STC value are such that, in accordance with the analysis conditions and the like, either one of these values may be selected or two or more of these values may be combined together. The conversion takes place as a processing of digital signals.

Subsequently, the converted signal is D/A-converted by a D/A converter 70, and mixed with a SYNC signal by another mixing circuit 72. The resultant image signal is outputted to the output terminal 75 provided for an external image analyzing apparatus, such as those described above, for performing texture analysis, again such as that described above. On the other hand, the image signal whose gain, contrast and STC have been adjusted by the adjusting circuit 63 is outputted, via the D/A converter 67 and the mixing circuit 68, to the external video monitor 74.

As described above, according to this embodiment, even if the observer has made changes in the gain, contrast and the STC signals of an output of the observation apparatus in order to observe an image, when image data is to be outputted to the associated image analyzing apparatus, image data in a state equivalent to the state before the changes by the observer can be obtained at the output terminal 75. Thus, it is possible to provide an ultrasonic observation apparatus for image analysis that is capable of outputting image data which: is advantageous to image analysis; has no risk of reducing the precision of analysis; and has highly precise reproducibility. The conversion performed by the data conversion circuit 69 need not recover the state before the adjustment by the adjusting circuit 63 and, instead, the conversion may be such that certain fixed values appropriate to the image analysis are always obtained.

Figure 11:
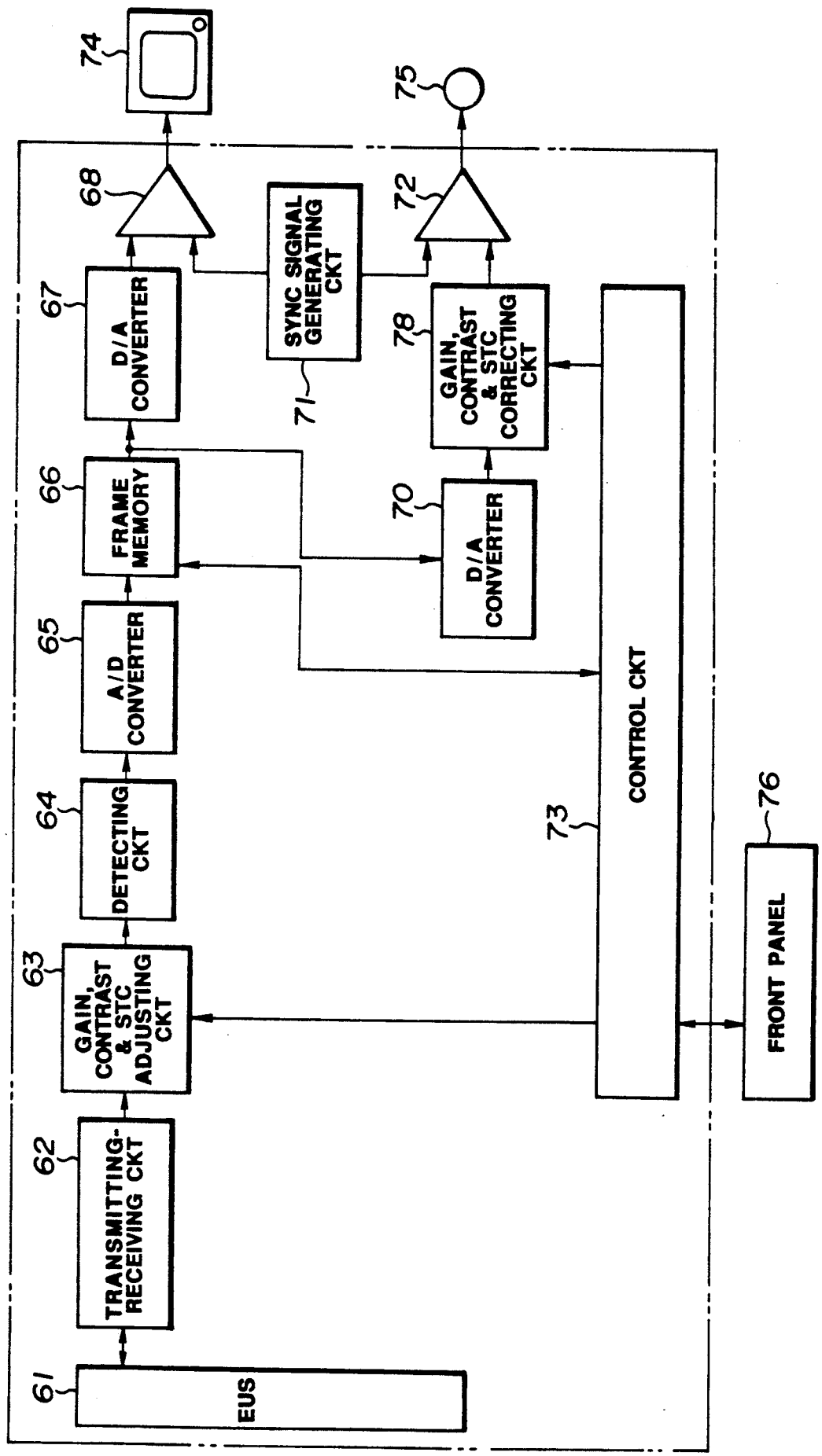
FIG. 11 is a structural block diagram of an ultrasonic observation apparatus, showing a fifth embodiment of the present invention.

FIG. 11 is a structural block diagram of an ultrasonic observation apparatus, showing a fifth embodiment of the present invention. The observation apparatus according to this embodiment is distinguished from that according to the fourth embodiment in the following points: Image data, stored in the frame memory 66 after changes have been made in the gain, the contrast and STC of the probe output, is fed to a D/A converter 70 where the data is D/A-converted. The resultant analog signal is supplied to a gain, contrast and STC correcting circuit 78, serving as a means for outputting an image signal for image analysis. The correcting circuit 78 performs, on the basis of a command of the control circuit 73, data conversion similar to that in the fourth embodiment, whereby the gain, the contrast, and the STC are corrected by the same magnitudes as those of the changes caused by the gain, contrast and STC adjusting circuit 63, and are thus allowed to recover their original values. The other circuit arrangement of the fifth embodiment is the same as that in the fourth embodiment.

The fifth embodiment is characterized in that both of the gain, contrast and STC adjusting circuit 63 and the correcting circuit 78 perform analog processing, thereby making it difficult for correction errors to occur.

Figure 12:
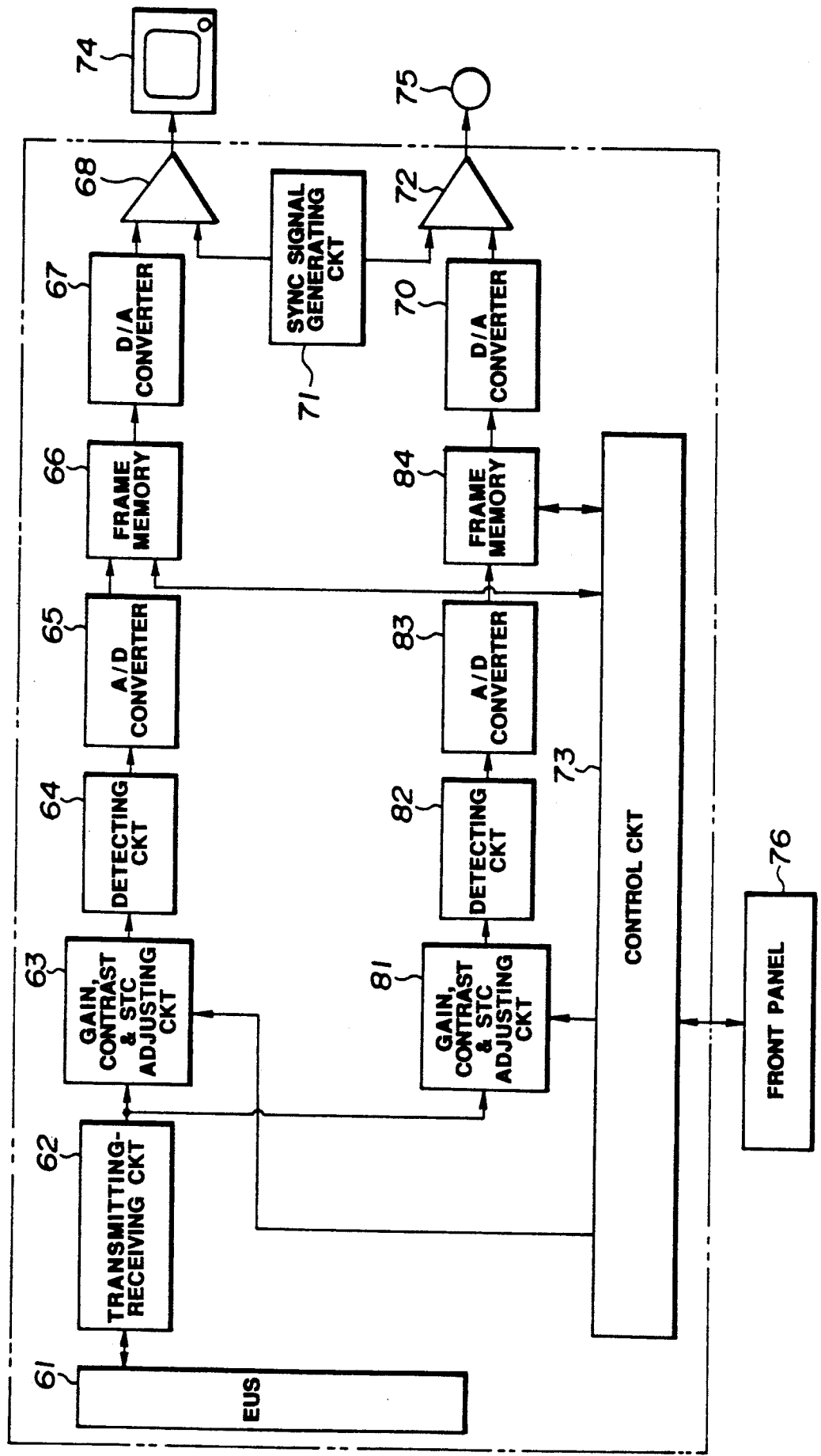
FIG. 12 is a structural block diagram of an ultrasonic observation apparatus, showing a sixth embodiment of the present invention.

FIG. 12 is a structural block diagram of an ultrasonic observation apparatus, showing a sixth embodiment of the present invention. The observation apparatus according to the sixth embodiment is distinguished from the apparatus according to the fourth embodiment in that a line for image displaying processes and a line for processing an image to be analyzed are provided independently from each other. The image displaying line is the same as that of the fourth embodiment. The analyzing image processing line includes, as shown in FIG. 12, a gain, contrast and STC adjusting circuit 81 which cannot be adjusted by the observer, and which processes tomographic image data from the transmitting-receiving circuit 62. The output of the adjusting circuit 81 is, similarly to that of the adjusting circuit 63 in the displaying line, detected by a detecting circuit 82, A/D converted by an A/D converter 83 and, after subjected to interpolation and the like, stored in a frame memory 84. During the processing of data for image analysis, image data from the frame memory 84 is D/A-converted by a D/A converter 70. Thereafter, the data is mixed with an output of a video SYNC signal generating circuit 71 by a mixing circuit 72, and outputted, as image data for analysis, at an output terminal 75 provided for an external image analyzing apparatus.

According to this embodiment, since a line for processing an image to be analyzed is provided independently, it is always possible to obtain image data which is different from the image data adjusted by the observer for the purpose of observation and which is advantageous to the image analysis.

Figure 13:
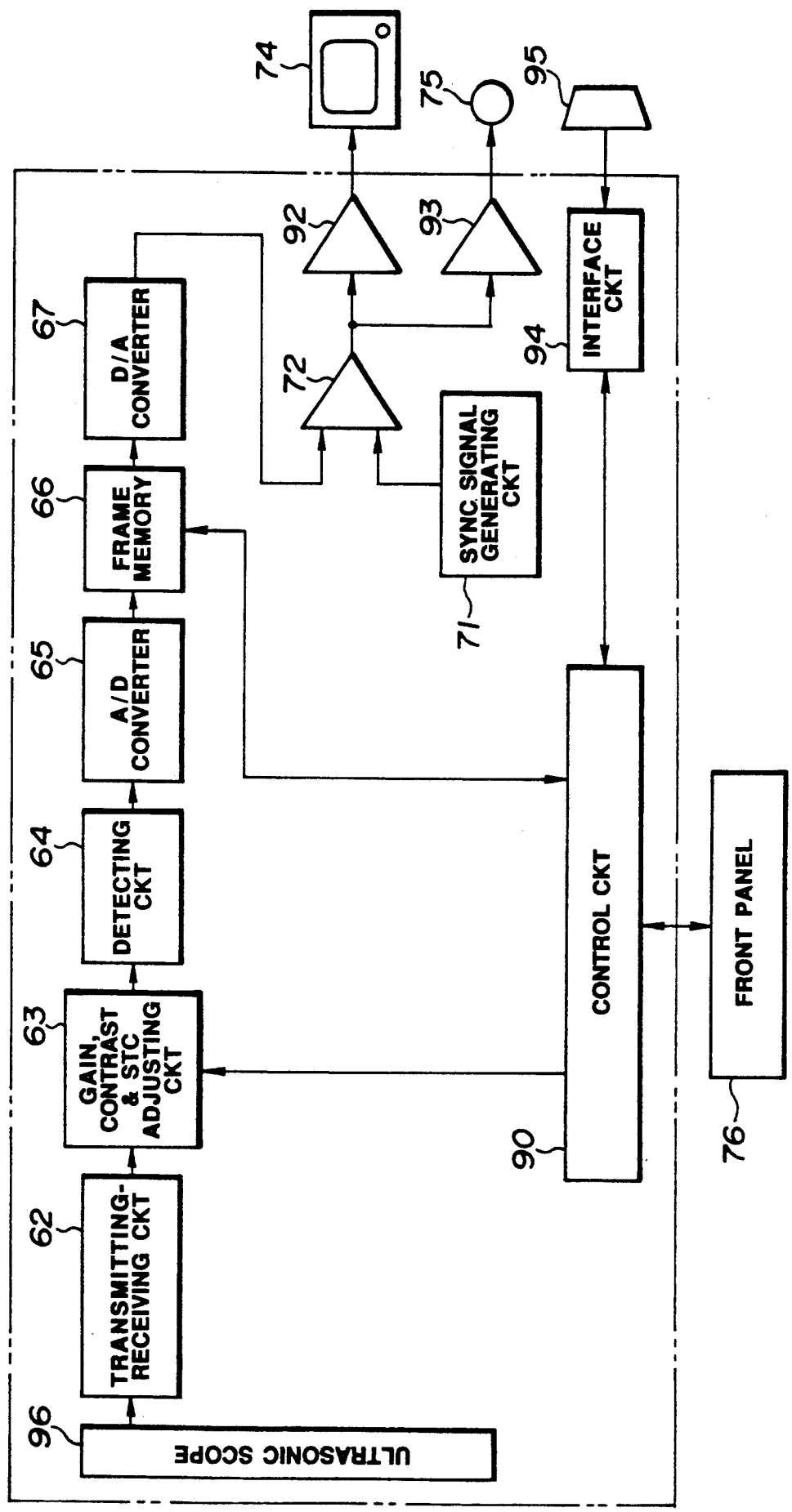
FIG. 13 is a structural block diagram of an ultrasonic observation apparatus, showing a seventh embodiment of the present invention.

FIG. 13 is a structural block diagram of an ultrasonic observation apparatus, showing a seventh embodiment of the present invention. This observation apparatus is distinguished from the apparatus according to the fourth embodiment in that the apparatus shown in FIG. 13 includes an interface circuit 94 providing an interface with an image analyzing apparatus, and that a gain, contrast and STC control signal is inputted from the image analyzing apparatus to a control circuit 90. By virtue of this arrangement, it is possible to cause a gain, contrast and STC adjusting circuit 63 to operate on the basis of the control signal so as to output image data for use in image analysis. In this embodiment, the measurement section comprises an ultrasonic scope 96. Further, a video output from a mixing circuit 72 is amplified by amplifying circuits 92 and 93, the amplified outputs being respectively outputted to a monitor 74 and an output terminal 75 for image analysis. The interface circuit 94 also enables communication with an external image analyzing apparatus via an input/output circuit 95.

According to this embodiment, since the gain, contrast and STC of an image data signal for use in image analysis are all the time controlled by an external image analyzing apparatus, it is possible to perform image analysis with a high level of precision. The interface circuit 94 may be provided in the external image analyzing apparatus.

Figure 14:
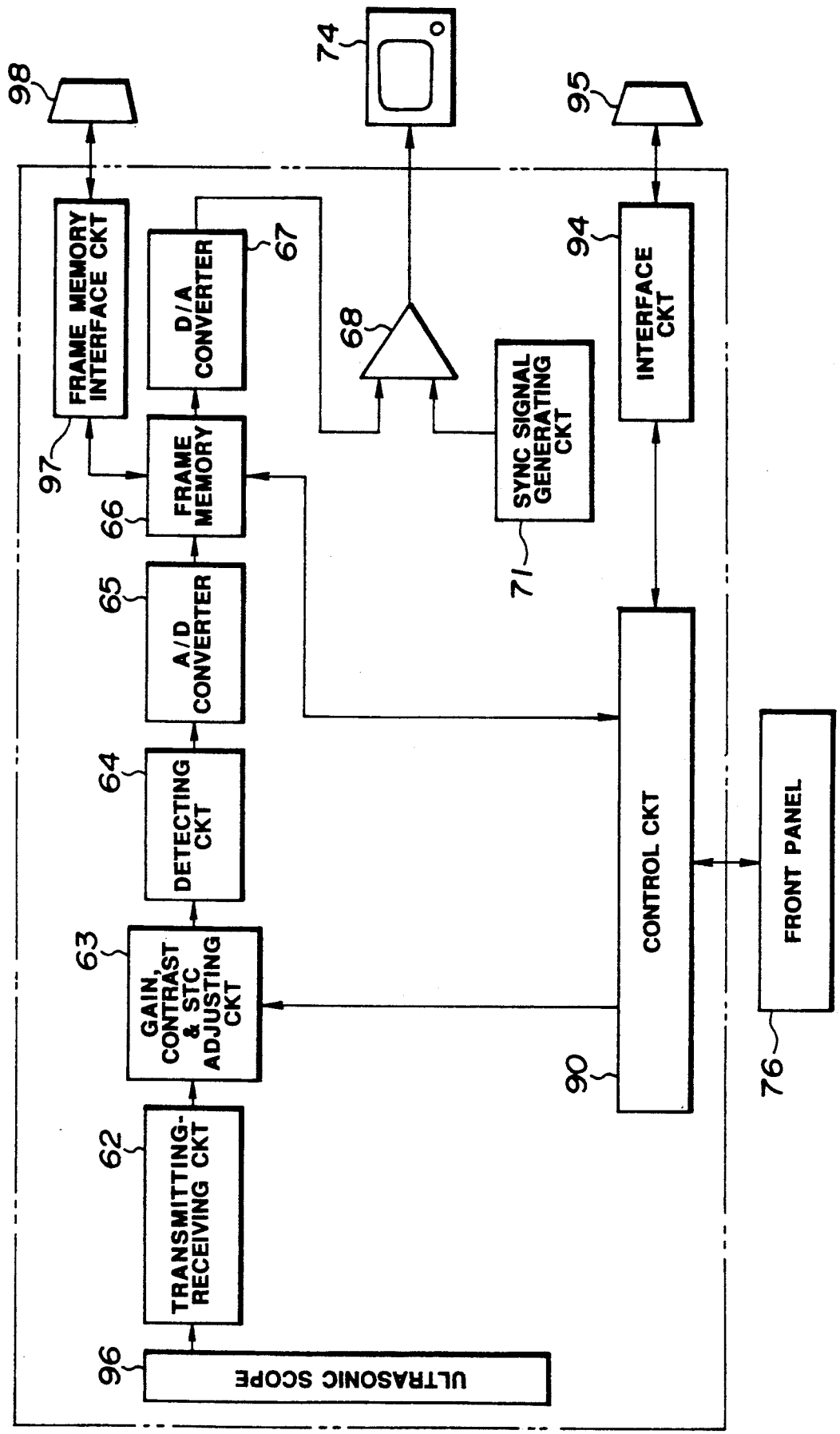
FIG. 14 is a structural block diagram of an ultrasonic observation apparatus, showing an eighth embodiment of the present invention.
Figure 15:
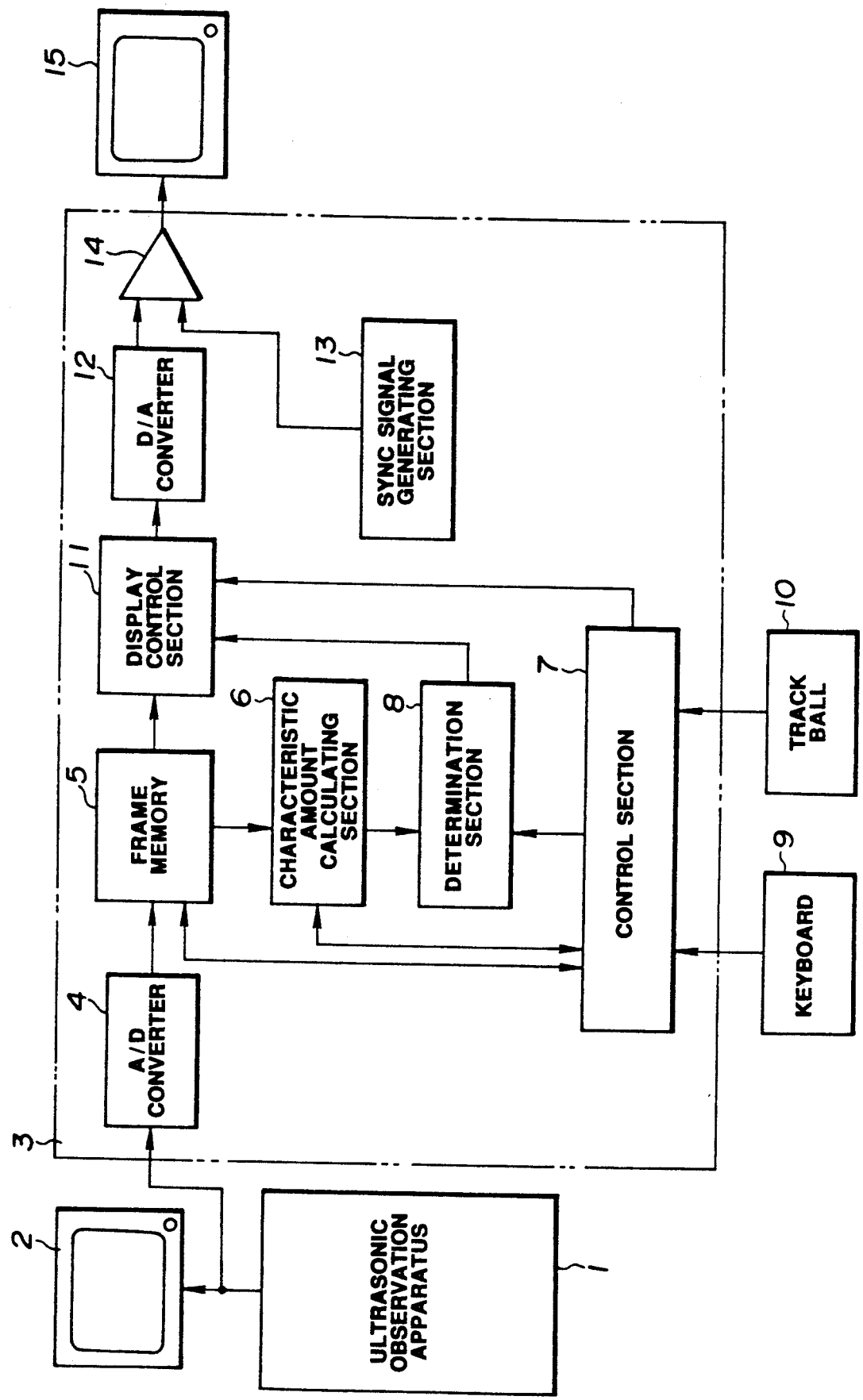
FIG. 15 is a structural block diagram showing an example of a conventional ultrasonic image analyzing apparatus.
Figure 16:
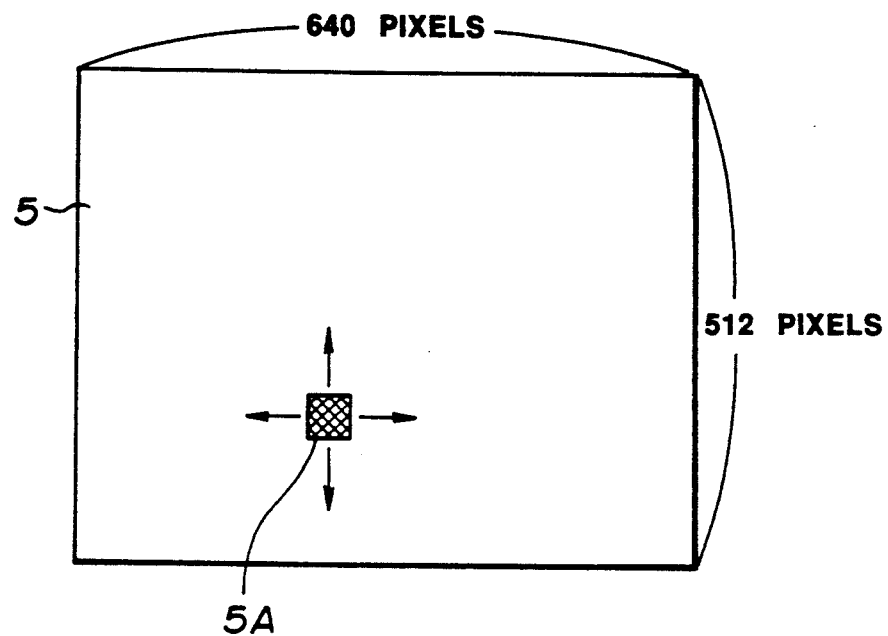
FIG. 16 is a diagram showing an example of the arrangement of pixels of a frame memory.
Figure 17:
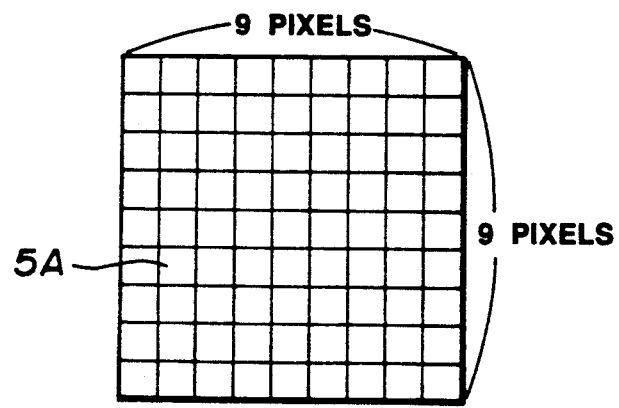
FIG. 17 is a diagram showing an example of the arrangement of pixels of one ROI.

FIG. 14 is a structural block diagram of an ultrasonic observation apparatus, showing an eighth embodiment of the present invention. The observation apparatus is distinguished from the apparatus according to the seventh embodiment in that a frame memory interface circuit 97 for the associated image analyzing apparatus is provided, so that image data for image analysis is directly transmitted as a digital signal from a frame memory 66 of the observation apparatus to the image analyzing apparatus. The observation apparatus also includes an input/output circuit 98 for the frame memory interface circuit 97. In the apparatus shown in FIG. 14, a signal for controlling gain, contrast and STC into values appropriate to image analysis, and like signals are inputted from the image analyzing apparatus via an interface circuit 94 to a control circuit 90, so that, on the basis of the control signal, a gain, contrast and STC adjusting circuit 63 is operated. The control circuit 90 also controls data input/output as well as address input with respect to the frame memory 66. According to this embodiment, image data from the frame memory 66 can be outputted while being maintained in the form of a digital signal, thereby enabling analysis to be performed with a higher level of precision without involving the risk of deteriorating the signal.

In each of the fourth to eighth embodiments, data stored in the frame memory 66 or 84 is image information for use in analysis. However, apparatuses to which the present invention may be applied are not limited to those adapted to process image information, but, of course, include apparatuses adapted to process digital information for use in in-frame analysis.

What is claimed is:

1. An ultrasonic image analyzing apparatus in an ultrasonic diagnosis system, said apparatus performing, on the basis of observation image information outputted from an ultrasonic observation apparatus, image analysis of an observation-object portion being observed, said image analyzing apparatus comprising:

an image information storing means for inputting image information on said observation-object portion obtained by performing scanning with an ultrasonic probe, and for storing said image information;

a parameter storing means for storing a plurality of parameters for image analysis which correspond to the measurement environment of said ultrasonic observation apparatus and/or said observation-object portion;

an image analysis control means for automatically selecting, from among said plurality of parameters, those parameters appropriate to the measurement environment, either automatically or manually specified, and/or said observation-object portion, and for specifying regions of interest (ROIs) on a plane of an image of said observation-object portion; and a characteristic amount calculating means for calculating characteristic amounts indicative of the structure and the properties of said observation-object portion by analyzing, using said selected parameters, said image of said observation-object portion with respect to each of said ROIs.

2. An ultrasonic image analyzing apparatus according to claim 1, wherein said measurement environment is determined by the ultrasonic probe of an ultrasonic scope used in said ultrasonic observation apparatus which generates said image information to be inputted, said probe indicating the type of said ultrasonic scope.

3. An ultrasonic image analyzing apparatus according to claim 1, further comprising a scope identifying means for automatically identifying the type of an ultrasonic scope such as that described in claim 2.

4. An ultrasonic image analyzing apparatus according to claim 1, wherein said observation-object portion is an observation-object portion and/or an object organ of the body which is depicted through a body mark display means and which is already specified on the basis of display on said body mark display means.

5. An ultrasonic image analyzing apparatus according to claim 1, capable of performing image analysis by causing said image analysis control means to vary said parameters and/or said ROIs in correspondence with the directions in which the ultrasonic wave from said ultrasonic probe propagates, wherein said image information storing means stores information on an image of said observation-object portion obtained by performing radial scanning with said ultrasonic probe.

6. An ultrasonic image analyzing apparatus in an ultrasonic diagnosis system, said apparatus performing, on the basis of observation image information outputted from an ultrasonic observation apparatus, image analysis of an observation-object portion being observed, said image analyzing apparatus comprising:

an image storing means for storing image information on said observation-object portion obtained by performing radial scanning with an ultrasonic probe;

an image analysis control means for specifying at least one of parameters for image analysis and ROIs while varying at least one of said parameters and said ROIs in correspondence with directions in which ultrasonic waves from said ultrasonic probe propagate; and a characteristic amount calculating means, operably coupled to said image storing means and said image analysis control means, for calculating characteristic amounts indicative of the structure and the properties of said observation-object portion and for analyzing, by using said varied parameters for image analysis, an image of said observation-object portion with respect to each of said varied ROIs of said observation-object portion to thereby perform image analysis while at least one of said parameters and said ROIs is varied.

7. An ultrasonic image analyzing apparatus according to claim 6, wherein said ROIs are controlled by said image analysis control means in such a manner that at least one of the size and shape of said ROIs is varied in the radial directions of said radial scanning with said probe.

8. An ultrasonic image analyzing apparatus according to claim 6, wherein said image analysis control means scans said ROIs on the plane of the observation image in the direction corresponding to the direction of said radial scanning with said probe.

9. An ultrasonic image analyzing apparatus according to claim 6, wherein said image analysis control means scans said ROIs in such a manner that the feed amount per parameter-calculation is varied in correspondence with the directions in which the ultrasonic wave from said probe propagates.

10. An ultrasonic observation apparatus in an ultrasonic diagnosis system, said apparatus supplying observation image information for image analysis to an ultrasonic image analyzing apparatus for performing image analysis of an observation-object portion being observed, said ultrasonic observation apparatus comprising:

a gain, contrast and sensitivity time control (STC) adjusting means for inputting image information on said observation-object portion obtained by performing scanning with an ultrasonic probe, said means adjusting the gain, the contrast and the STC of said image information while the scanning with said ultrasonic probe is performed; and an image signal outputting means, operably coupled to said STC adjusting means, for outputting said image information as image information in which at least one of said gain, said contrast and said STC is in one of an unadjusted state and an adjusted state.

11. An ultrasonic observation apparatus according to claim 10, wherein said image signal outputting means converts said image information resulting from processing by said gain, contrast and STC adjusting means while said image information is in the form of a digital signal or an analog signal, so as to cause said image information to be again outputted as said image information having said unadjusted state or said adjusted state.

12. An ultrasonic observation apparatus according to claim 10, wherein said image signal outputting means comprises a circuit forming a line different from the line incorporating said gain, contrast and STC adjusting means.

13. An ultrasonic observation apparatus according to claim 10, wherein said gain, contrast and STC adjusting means also serves as said image signal outputting means, and is controlled via a communication interface with said external ultrasonic image analyzing apparatus, thereby enabling said image information having said unadjusted state or said adjusted state to be outputted.

* * * * *